United States Patent [19]
Jennings et al.

[11] Patent Number: 5,735,862
[45] Date of Patent: Apr. 7, 1998

[54] SEMI-AUTOMATIC SUTURING AND SEWING DEVICE

[76] Inventors: Erwin Reeves Jennings, 4029 Riverside Dr., Brunswick, Ga. 31520; Jaime D. B. Klatt, 643 Crispen Blvd., Brunswick, Ga. 31525

[21] Appl. No.: 717,923

[22] Filed: Sep. 23, 1996

[51] Int. Cl.⁶ ............................................. A61B 12/04
[52] U.S. Cl. ................................... 606/147; 112/169
[58] Field of Search ............................ 606/144–148; 112/169

[56] References Cited

U.S. PATENT DOCUMENTS

| | | | |
|---|---|---|---|
| 1,131,163 | 3/1915 | Saunders et al. | 606/147 |
| 1,155,378 | 10/1915 | Steedman | 606/147 |
| 2,434,133 | 1/1948 | Volk . | |
| 2,580,964 | 1/1952 | Skaller . | |
| 2,601,564 | 6/1952 | Smith | 606/147 |
| 2,646,045 | 7/1953 | Priestley . | |
| 4,123,982 | 11/1978 | Bess, Jr. et al. . | |
| 4,235,177 | 11/1980 | Arbuckle . | |
| 4,236,470 | 12/1980 | Stenson | 112/169 |
| 4,414,908 | 11/1983 | Eguchi et al. | 112/169 |
| 4,417,532 | 11/1983 | Yasukata | 112/169 |
| 4,440,171 | 4/1984 | Nomoto et al. | 606/145 |
| 4,553,544 | 11/1985 | Nomoto et al. | 606/148 |
| 4,635,638 | 1/1987 | Weintraub et al. . | |
| 4,747,358 | 5/1988 | Moll et al. . | |
| 5,100,421 | 3/1992 | Christoudias . | |
| 5,389,103 | 2/1995 | Melzer et al. . | |
| 5,454,919 | 10/1995 | Knoepfler | 606/147 |
| 5,477,794 | 12/1995 | Klundt . | |
| 5,480,406 | 1/1996 | Nolan et al. . | |
| 5,496,334 | 3/1996 | Klundt et al. . | |
| 5,645,552 | 7/1997 | Sherts | 606/147 |

FOREIGN PATENT DOCUMENTS 2 260 704   4/1993   United Kingdom .

OTHER PUBLICATIONS

Article entitled "A New Two–Way Needle For Blood Vessel Anastomosis" by Jennings et al., Jul. 1, 1954.
Brochure entitled "Endoscopic suturing made easy"—Endo Stitch 10mm Suturing Device, Auto Suture Company (division of U.S. Surgical Corp.), 1994.

*Primary Examiner*—Gary Jackson
*Attorney, Agent, or Firm*—Banner & Witcoff, Ltd.

[57] ABSTRACT

A semi-automatic suturing device passes a single or double pointed needle back and forth between two needle holders in order to avoid the need for manually grasping and otherwise manipulating the needle after it has passed through body tissue or other material being sewn. The needle holders are provided in the form of respective sets of vise-like jaws on a pair of arms which are pivotally attached to each other. The holders are thereby manually movable into and out of proximity with each other. The needle holding jaws are automatically alternatingly actuated to open and close when they are pivoted into proximity with each other, such that a hand-off of the needle can occur. Actuation of the needle gripping jaws is power driven, e.g., by a solenoid, and automatically initiated by a proximity switch which detects when the jaws have been brought together. Logic circuitry ensures that one set of needle gripping jaws does not release the needle until the other holder has closed to grip the opposite end of the needle. In this manner, accidental needle droppings are avoided.

18 Claims, 7 Drawing Sheets

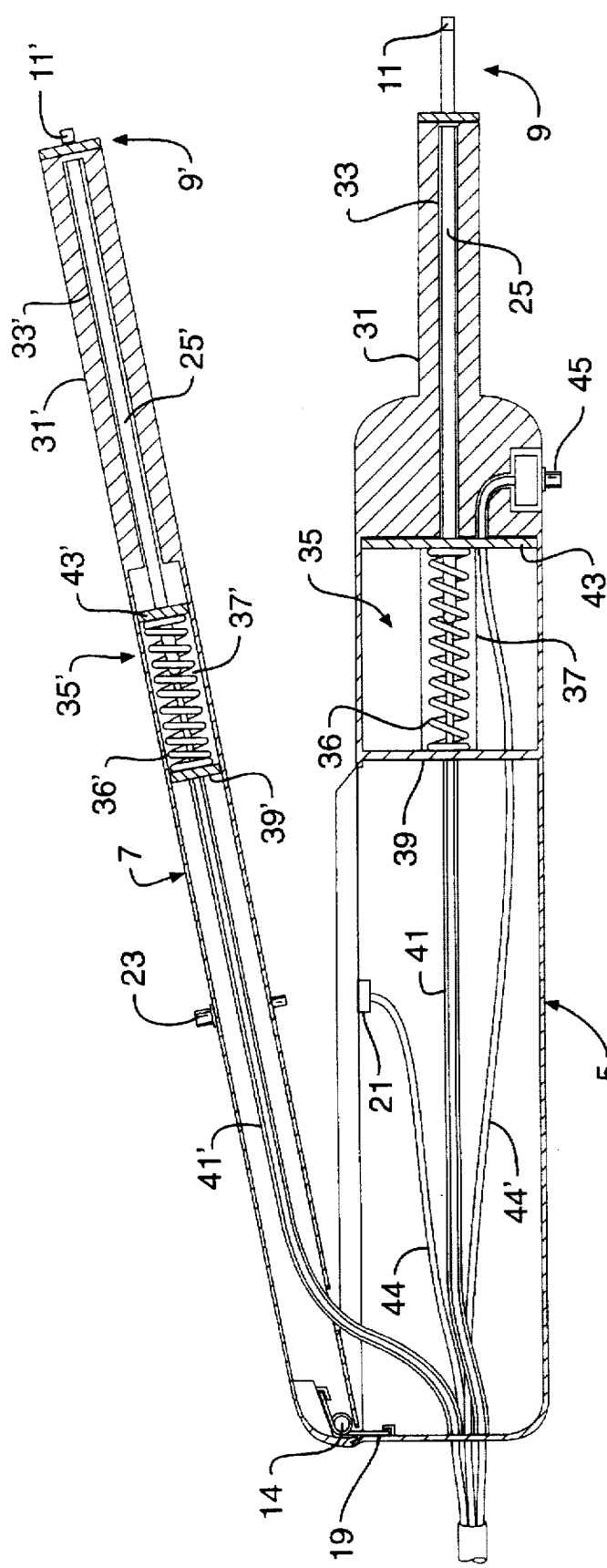
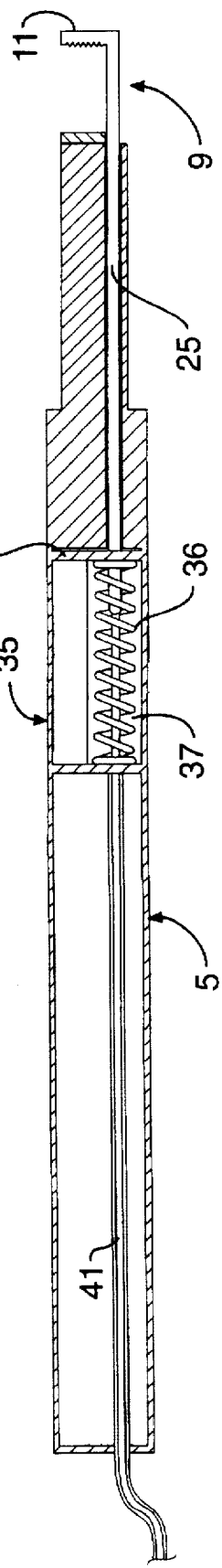
FIG. 5
FIG. 6

SEMI-AUTOMATIC SUTURING AND SEWING DEVICE

BACKGROUND OF THE INVENTION

The present invention relates to suturing and sewing devices. In particular, the present invention concerns hand operable apparatus for facilitating traditionally manual suturing/sewing operations, in both medical and non-medical environments.

Traditionally, suturing in the medical profession has been a wholly manual procedure. Typically, adjacent edges of tissue layers to be joined are clamped or otherwise held in closely adjacent or overlapping relation. A needle and attached thread are then repeatedly passed through the adjoining tissue layer edges. The latter step is effected by securing the needle in a finger actuated pliers-like clamp and pushing the needle into the tissue, allowing the pointed distal end to protrude from the opposite side. Next, the protruding distal end of the needle is grasped and the needle is pulled completely through the tissue. Depending on the stitch being utilized, the needle may then be reoriented to repeat the procedure in the opposite direction, or returned to the starting side (with the thread passing over the seam line), for a repeat of the procedure. Advantageously, in the case of a double pointed needle (with the thread attached at a midpoint between the pointed ends), the needle can be passed back and forth through the tissue, from one side to the other, without an end-to-end reorientation of the needle. With all of the above-mentioned variations, the steps are repeated to create the required number of stitches, and finally the ends of the thread are knotted to complete the suture.

Performance of the above-described traditional techniques typically requires the use of two hands. In many instances, it is necessary that the physician have one hand free for other purposes during the suturing procedure, in which case it is necessary to utilize the hand of an assistant in order to pull the needle through the tissue and pass it back to the doctor. Particularly when a large number of stitches are involved, suturing procedures become tedious, time consuming and fatiguing, to the obvious detriment of both the patient and the attending care givers. Moreover, over the long term, health care personnel performing suturing procedures on a regular basis may experience repetitive motion stress injury.

The traditional procedures utilized for medical suturing are not unlike the traditional manual techniques for sewing fabrics and the like. Like medical suturing, sewing by hand requires considerable dexterity. This may present a barrier to certain persons desiring to undertake such activity. For example, sewing by hand is a popular pastime activity amongst elderly persons, yet many are unable to perform the intricate hand work that is required due to arthritis and/or peripheral neuropathy disorders.

Numerous attempts have been to devise hand tools for improving upon the traditional completely manual suturing/sewing techniques.

Saunders et al. U.S. Pat. No. 1,131,163 and Steedman U.S. Pat. No. 1,155,378 disclose suturing devices comprising a pair of needle holders between which an arcuate needle is passed. Handles are provided for pivoting the needle holders together manually, and a separate movement of the handles is required in order to engage one of the holders with the needle, and release the other. Needle hand-off is performed when the holders are spaced apart from each other. A locking mechanism is provided for ensuring that the needle is not released from one holder unless the other holder is in position to receive the opposite end of the needle.

Stenson U.S. Pat. No. 4,236,470 discloses a pair of arms pivoted together at one end and having needle holders at their opposite ends movable into and out of proximity with each other to effect the hand-off of a double pointed needle. The main embodiment has separate spring loaded triggers for manually actuating the opening and closing of the respective needle holders. A second embodiment discloses a single trigger for simultaneously releasing the needle from one holder and engaging it with the other.

Weintraub et al. U.S. Pat. No. 4,635,638 teaches power (pneumatic) actuation of a pair of needle gripping members mounted on rectilinearly extendable and retractable arms. Separate switches are provided for each arm and associated gripping member. By advancing the switches through a series of positions, the arms are first extended, and then the gripping jaws are actuated to close; a reverse movement of the switches causes the associated gripping jaw to open, and then retraction of the associated arm.

Nolan et al. U.S. Pat. No. 5,480,406 ("the '406 patent") is a U.S. Surgical Corp. patent referring to its commercially available Endo Stitch device. The patent also mentions related U.S. Surgical patent applications (now abandoned) directed to the device. The Endo Stitch device has a pair of manually operated handles serving to open and close a pair of needle holding jaws located at the end of an elongated arm. Each jaw incorporates a needle holding recess, and a needle is passed from one to the other. A manually rotatable actuating member with a pair of tabs for finger manipulation serves to simultaneously engage a needle in one holder and release the needle from the other holder, once the jaws have been closed by operation of the separate handle. A safety mechanism is provided to prevent the release of a needle gripping holder unless the jaws are in their closed position such that the other holder can grasp the needle.

Smith U.S. Pat. No. 2,601,564 discloses a suturing device having two arms which are independently, rectilinearly extensible and retractable to effect a needle hand-off. The arms comprise tubular members with grooves in their respective ends. Rods are rotatable within the tubes in order to release and grip the needle. Respective spring-loaded levers move first longitudinally to extend the arms, then vertically to effect rotation in order to clamp the needle.

Melzer et al. U.S. Pat. No. 5,389,103 discloses an endoscopic suturing device with one stationary and one movable mouthpiece for passing therebetween a double pointed needle. The movable mouthpiece is moved linearly with respect to the stationary mouthpiece by way of concentric tubes. The device is semi-automatic. A foot switch connected with a pneumatic power source opens and closes the jaws of the stationary mouthpiece. The jaws of the other mouthpiece are spring-loaded to grip and release the needle.

In summary, the above references disclose suturing devices with various means for effecting transfer of a needle back and forth between gripping elements movable with respect to each other. Some of the devices are completely manual, while others include power actuation. The completely manual devices require multiple hand motions, and the exertion of considerable actuating forces, thus leading to hand fatigue. While the powered devices would apparently reduce the required manual effort, those devices still require inconvenient coordinated movements and/or switch actuations to effect needle hand-off. Moreover, the known powered devices in particular appear susceptible to inadvertent needle droppings due to premature needle release.

Published U.K Patent Application GB 2 260 704 A discloses a laparoscopic suturing device with an overall structure which is generally similar to the U.S. Surgical Endo Stitch device. In the embodiment shown, a pair of jaw elements are pivoted to each other at the end of an elongated arm. Each jaw element has a needle retaining recess. A manual trigger is squeezed to first bring the jaws together and then actuate respective securing means to release the needle from one jaw and grip it with the other. The document mentions the possibility of powered actuation of the securing means by hydraulic, pneumatic or electrical (e.g., solenoid) means. While this device apparently would avoid the need for discrete hand movements for bringing the jaws together, then actuating the securing means to effect a needle transfer (as required by the Endo Stitch device), the disclosed utilization of a single motive force (either manual or powered) for actuating these tool motions would likely cause difficulties in controlling both the movement of the jaws and the needle gripping/release actions. Moreover, the disclosed design of the illustrated dual purpose mechanical linkage is rather conceptual and appears susceptible to operability problems.

SUMMARY OF THE INVENTION

In view of the foregoing it is a principal object of the present invention to provide a relatively simple and reliable hand operable tool that effectively minimizes the amount of time, effort and dexterity required to perform suturing and sewing operations.

It is a particular object of the present invention to provide a semi-automated suturing/sewing device that does not require separate hand motions in order to first bring a pair of needle holders into a needle transfer position and then to effect a needle transfer.

It is a further object of the invention to provide a simple design that avoids the above-mentioned required separate hand motions, yet retains a high degree of controllability.

It is yet another objective of the present invention to provide a semi-automatic suturing device with a simple and effective safety mechanism for preventing inadvertent needle drops due to premature needle holder release.

These and other objects are achieved by a semi-automatic suturing/sewing device in accordance with the present invention. The device has a hand graspable tool body. A pair of needle holders are operably connected to the body for movement with respect to each other, into and out of a preset needle transfer position, by application of manual force. Each needle holder has a releasable needle gripping element. A power actuator assembly provides motive forces, separate from the manual force, for actuating the gripping elements to move between respective needle gripping and release positions, and for providing a predetermined gripping force of said gripping elements in their respective gripping positions. An electronic control mechanism is provided for controlling operation of the power actuator assembly. The mechanism comprises a detector for producing a first signal when the needle holders have been moved to the needle transfer position. The control mechanism actuates the power actuator assembly in response to the first signal, to automatically alternatingly hold the gripping elements in their gripping positions and move the gripping elements to their release positions, in order to effect successive needle transfers from one needle holder to the other.

These and other objects, advantages and features of the present invention will be readily apparent and fully understood from the following detailed description of the preferred embodiments, taken in connection with the appended drawings.

BRIEF DESCRIPTION OF THE DRAWINGS

FIG. 5 is a horizontal cross-sectional view taken on line 5—5 in FIG. 3.

FIG. 6 is a cross-sectional view taken on line 6—6 in FIG. 2.

DETAILED DESCRIPTION OF THE PREFERRED EMBODIMENTS

Figure 1:
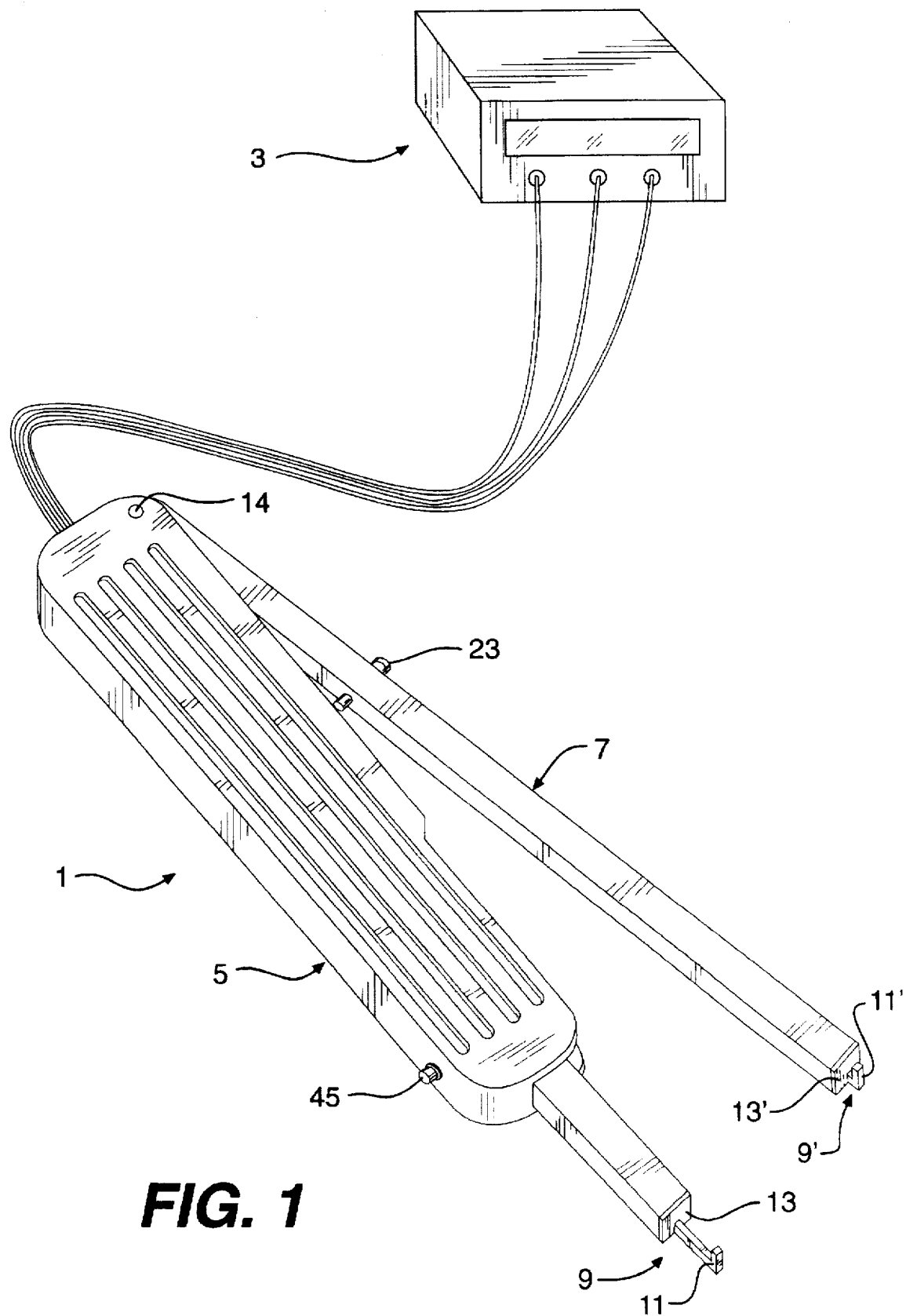
FIG. 1 is a perspective view of a semi-automatic suturing/sewing device in accordance with the present invention, having a hand graspable tool body (with arms thereof pivoted apart), and a separate control box.

Referring first to FIG. 1, a semi-automatic suturing/sewing device in accordance with the present invention includes a hand graspable tool body 1 and a separate control box 3. Tool body 1 comprises two elongated arms which are pivotally mounted to each other, a primary arm 5 and a secondary (smaller) arm 7. Each of arms 5, 7 carries at its end a vise-like needle holder 9,9' comprising a releasable needle gripping element in the form of a movable vise jaw 11, 11'. As illustrated in FIG. 1, needle holder 9 is in an extended, needle release position, spaced apart from an abutting clamp surface 13. Needle holder 9' is in a retracted needle gripping position, wherein jaw 11' is held tightly against a corresponding abutting clamp surface 13'.

Figure 2:
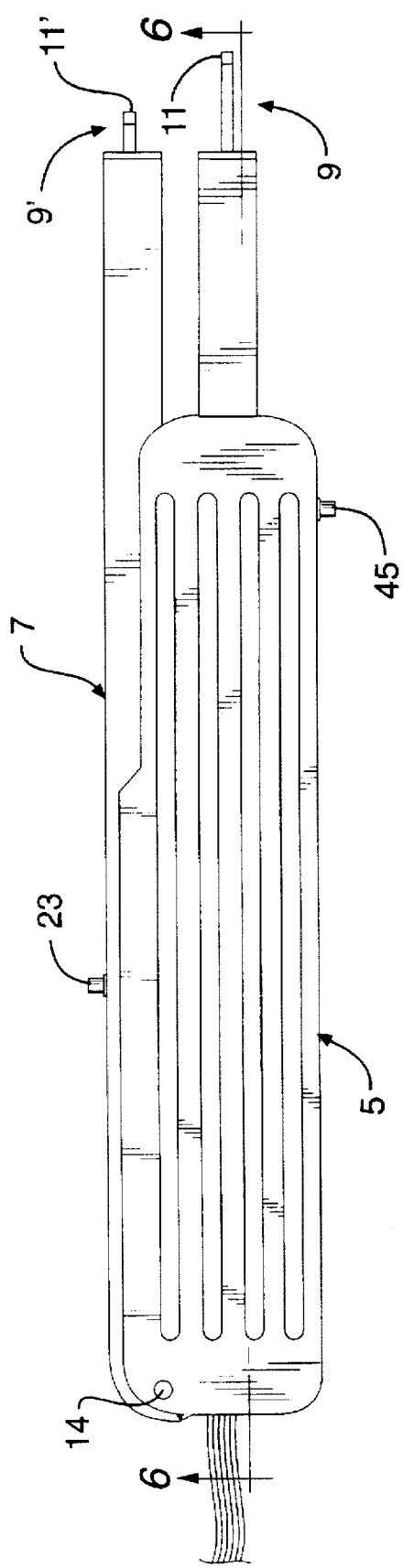
FIG. 2 is a top view of the tool body shown in FIG. 1, with the arms pivoted together to place a pair of needle holders in a needle transfer position.
Figure 3:
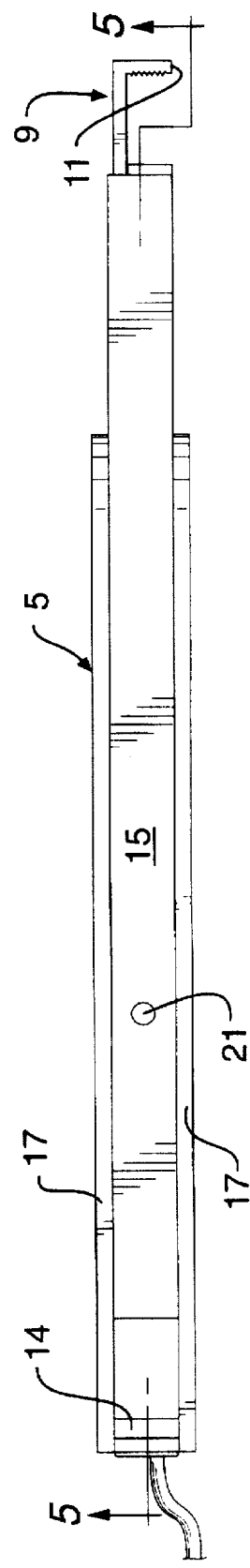
FIG. 3 is a side elevational view of a primary arm of the hand graspable body, clearly showing a slot for receiving a secondary (smaller) arm pivotally attached thereto.

As best seen in FIGS. 2–3, secondary arm 7 is pivotally mounted to primary arm 5 by a pivot pin 14, to move, by hand force, into and out of a channel 15 defined between a pair of spaced flanges 17 extending longitudinally along one side of a relatively wide proximal part of primary arm 5. Preferably, as seen in FIG. 5, arm 7 is biased to pivot away from arm 5 to a separated position established by abutting stop surfaces of the arms. As shown, the bias is provided by a torsion spring 19 mounted about pivot pin 13. The separated position of the arms allows a needle held in the needle holder of the other arm to be pressed through tissue or other material until the point of the needle protrudes from the other side. Pivoting the arms together positions needle holders 9, 9' in close proximity to each other, whereupon the released needle holder is automatically moved to a gripping position clamped down on the protruding end of the needle. Shortly thereafter, the gripping holder on the other side is caused to open and thereby release the needle. In this manner, a needle transfer from one to the other needle holder can be carried out, thus allowing the needle to be pulled through the tissue or other material with minimal hand movements and exertion, and without the necessity of a second hand.

The occurrence of an automatic needle transfer, upon moving holders 9.9' into close proximity with each other, is initiated by a proximity switch assembly including cooperative elements mounted on arms 5 and 7, respectively. As seen in FIGS. 3 and 5, mounted generally flush within channel 15 is a conventional spring-biased push-button type on-off switch 21. As seen in FIGS. 1 and 2, mounted at a corresponding location on arm 7 is an actuator pin 23 serving to depress and thereby actuate switch 21 as secondary arm 7 pivots into proximity with primary arm 5. The protruding distance of pin 23 is preferably made adjustable in order to allow adjustment of the relative positions of needle holders 9, 9' at which needle transfer occurs. This can be accomplished by various known means such as providing pin 23 as an advanceable set screw.

Figure 4:
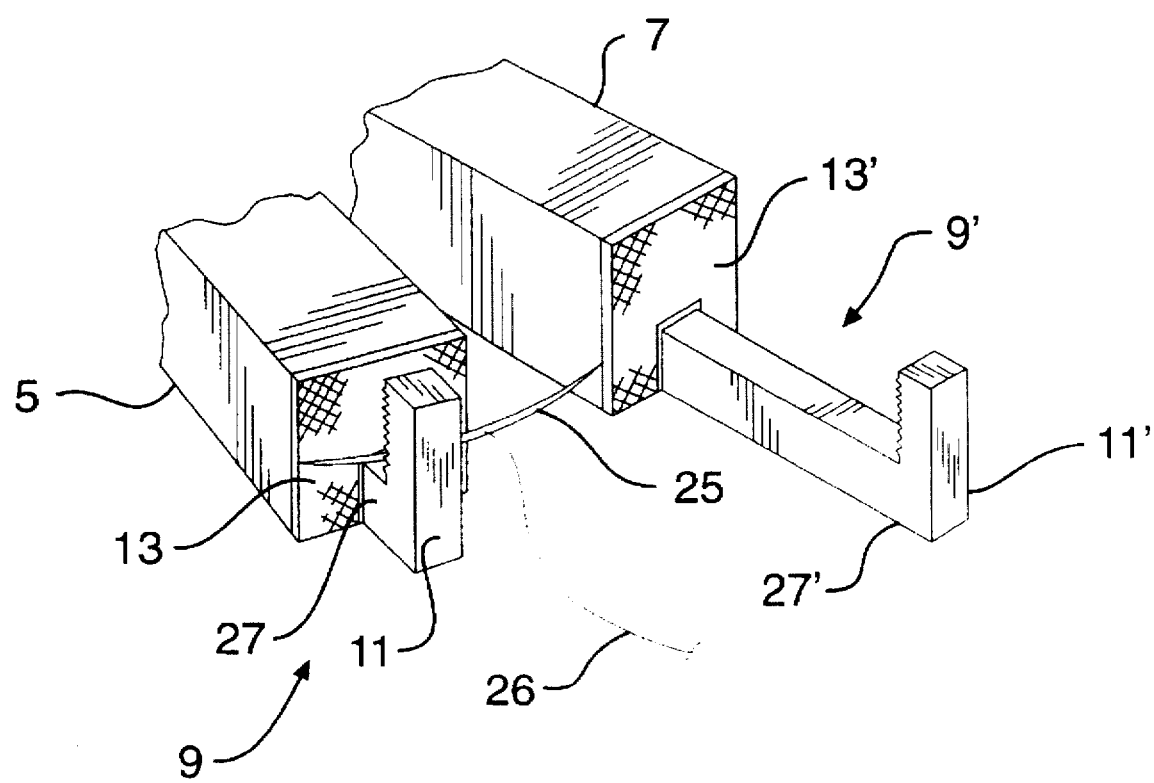
FIG. 4 is a close-up partial perspective view illustrating the vise-like needle holders of the inventive device.

Referring now to FIG. 4, the structure of needle holders 9, 9' is clearly seen, with needle holder 9 gripping a bowed double pointed needle 25 having a thread 26 attached at its midpoint. Releasable gripping jaws 11, 11' are preferably cast of or machined from surgical steel or the like, together with an elongated shank 27, 27' mounted for longitudinal movement within a respective one of arms 5, 7. The gripping faces of jaws 11, 11' are preferably knurled with a small diamond shaped pattern for securely gripping needle 25, as are the opposing clamp surfaces 13, 13' provided on the ends of arms 5,7. Preferably, tool body 1, including arms 5 and 7, will be molded of lightweight high impact plastic material, or the like. As shown, plates of surgical steel or other wear resistant material can be mounted on the ends of the plastic arms in order to provide clamp surfaces 13, 13'.

The illustrated arrangement of vise-like needle holders 9, 9' works perfectly well for gripping and allowing the transfer of various known types of needles, e.g., double point and single point, straight and bowed. Advantageously, in the case of a single point needle with the thread trailing from the tail end, the tool may be utilized with gripping jaws 11, 11' pointing downwardly, whereby trailing thread 26 will fall freely away from shanks 27, 27' as the tool is reoriented between stitches to redirect the needle point. Although the illustrated embodiment utilizes a simple arrangement for pivoting arms 5, 7 together in a single plane, it will be appreciated that for a bowed needle some advantage could be gained by providing a hinge arrangement that would provide the arms with a compound motion allowing the approaching needle holder to follow the arc of the needle shank.

Referring now to FIGS. 5 and 6, the structure of tool body 1 is further described. The distal ends of arms 5 and 7 are configured as blocks 31, 31' defining respective slot-like guide ways 33, 33' slidably receiving elongated jaw shanks 25, 25'. The jaw shanks extend beyond blocks 31, 31' in the proximal direction, into respective return spring sections 35, 35'. Each return spring section comprises a coil compression spring 36, 36' retained within a channel 37, 37' and abutted at its proximal end against a bracing wall 39, 39'. The end of each jaw shank 25, 25' is connected to a flexible control cable 41, 41' extending out of tool body 1 and to remotely located control box 3. Each shank 25, 25' carries a flange 43, 43' providing a push surface abutting with the distal end of the associated spring. By means to be described, control cables 41, 41' are drawn in the proximal direction, against the bias of springs 36, 36', to pull jaws 11, 11' into gripping engagement with abutting clamp surfaces 13, 13', and then released, in an alternating fashion. Rapid return of the jaws to a release position is assured by spring sections 35, 35'.

In addition to push-button switch 21, primary arm 5 carries a second switch 45 of conventional construction serving to initialize operation of the device. Signal wires 44, 44' from each of the switches extend out of tool body 1 to control box 3.

Figure 7:
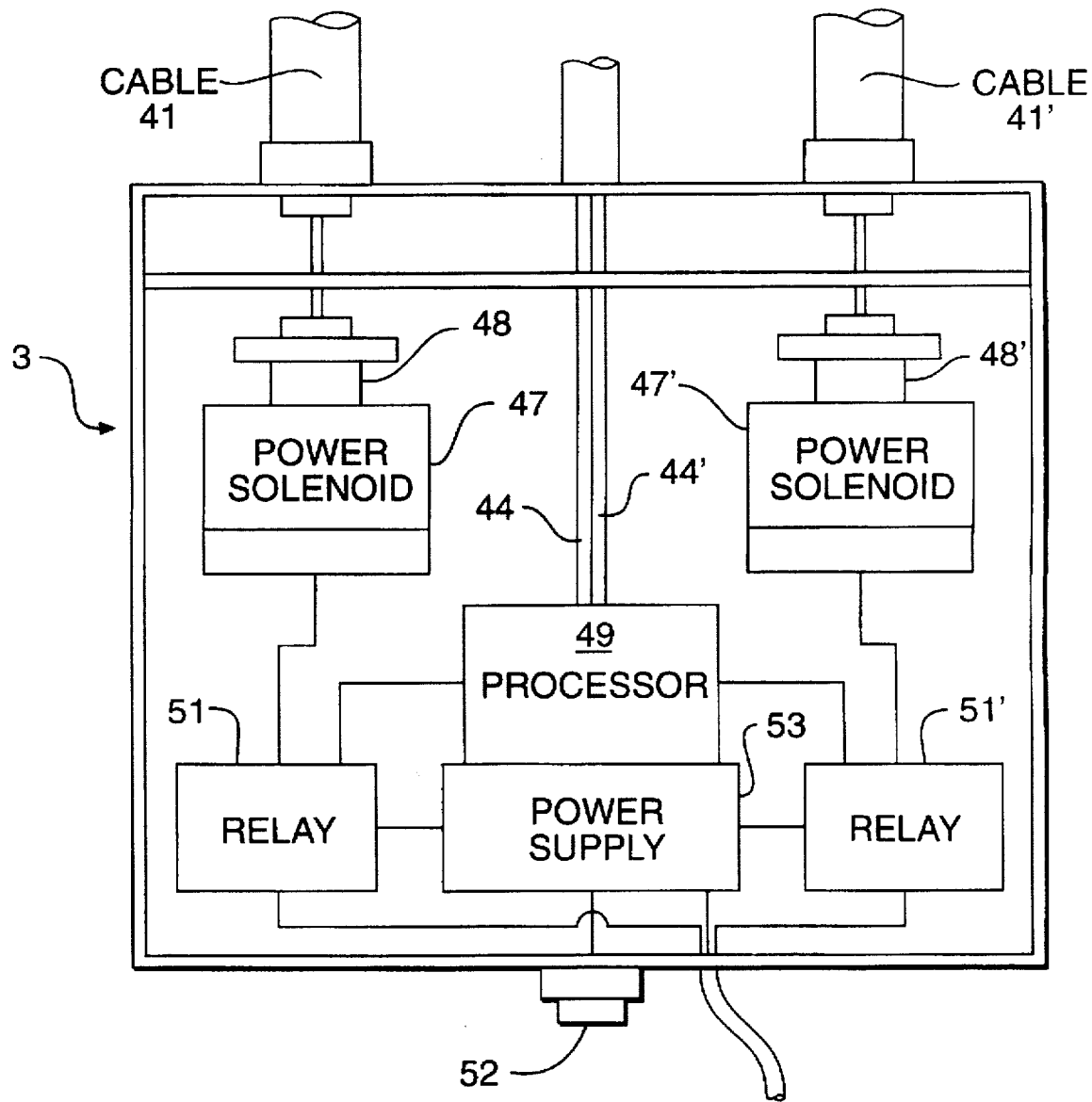
FIG. 7 is a schematic depiction of the circuitry and electro-mechanical componentry of the control box shown on FIG. 1.

Referring now to FIG. 7, it can be seen that control box 3 houses a power actuator assembly and an electronic control mechanism for controlling operation of the same. The power actuator assembly comprises a pair of power solenoids 47, 47' which are operably attached to the ends of control cables 41, 41'. In this manner, the in-and-out throw of each solenoid core 48, 48' is translated into a corresponding movement of the respective gripping jaw 11, 11' between its gripping and release positions. In addition, during activation of the solenoids, a strong gripping force, e.g., 40 lbs, is imparted to the needle holders 9, 9', In practice, the ideal gripping force level will depend on the particular sewing/suturing operation.

The electronic control mechanism preferably comprises a simple digital processor 49 which receives signals from switches 21 and 45 over lines 44, 44', and in response to those signals outputs a pair of control signals to a corresponding pair of electrical relays 51, 51'. Digital processor 49 receives conditioned low voltage DC power from a power supply 53 which receives and converts AC line voltage upon activation of power switch 52. On receipt of an ON signal from processor 49, relays 51, 51' close their contacts to supply the AC line voltage directly to the corresponding solenoids 47, 47', whereby the solenoid coils are energized causing retraction of the cores 48, 48'. The solenoid coils remain energized to impart a strong gripping force to the needle holders so long as the respective signals from processor 49 remain ON. When the signals switch to OFF, the relays are switched to deactivate the respective solenoids, whereupon the gripping jaws 11, 11' are caused to quickly move to an extended release position, under the bias of corresponding springs 36, 36'.

The preferred logic control of digital processor 49 is now described in greater detail. Upon actuation of initialization switch 45, the signal sent to processor 49 causes the processor to output an ON signal to one of relays 51, 51', and an OFF signal to the other. In this manner, e.g., gripping jaw 11 of primary arm 5 is caused to be held in its gripping position, thus securely holding a needle pre-positioned in needle holder 9. At the same time, gripping jaw 11' of secondary arm 7 remains in its release position. This operative position of the two jaws is maintained until a trigger signal is received from proximity switch 21, indicating that arms 5 and 7 have been pivoted together to bring needle holders 9, 9' into the needle transfer position. On receipt of a trigger signal, the output signals to relays 51, 51' flip-flop, causing gripping jaw 11 to move to its release position, and gripping jaw 11' to move (and be held in) its gripping position.

In order to prevent accidental needle droppings due to premature needle release, it is preferred that the logic control circuit introduce a time delay before switching its output signals from ON to OFF. More specifically, an OFF signal to one of the relays should only be generated after a predetermined time period following generation of a corresponding ON signal to the other relay. In this manner, it can be assured that release by one of needle holders 9, 9' will not occur before the needle has been securely gripped at its opposite end by the other. Programmability is desirable in order to allow this time delay to be preset at an empirically determined optimum value. Programmability is also desirable in order to allow introduction of a time delay between receipt of a trigger signal from proximity switch 21 and the generation of the corresponding output signals to the relays 51, 51'. This will allow the user to tailor the responsiveness of the device to his/her particular preferences.

It will be readily appreciated that a digital processor having the above-described functionality may be constructed from individual circuit components, as a special purpose integrated circuit chip and/or a suitably programmed general purpose computer. In a prototype device constructed by the inventors, a general purpose processor available from the Kayence company of Osaka, Japan (model no. KV-10R) was used with success. The processor was programmed using an associated software kit (model no. KV-3) and an IBM-type personal computer. Obviously, a special purpose circuit board or chip would be preferred for a commercial embodiment.

Figure 8A:
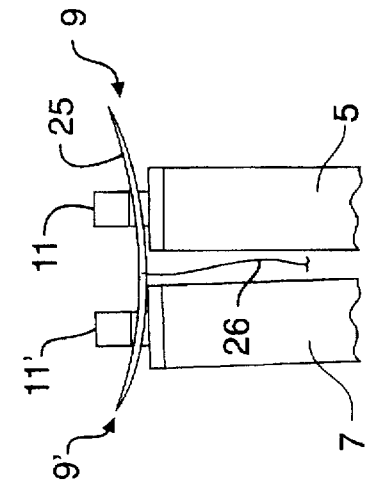
FIGS. 8A–8F are partial elevational views illustrating sequential stages of back-and-forth needle transfer operations with the inventive device.
Figure 8B:
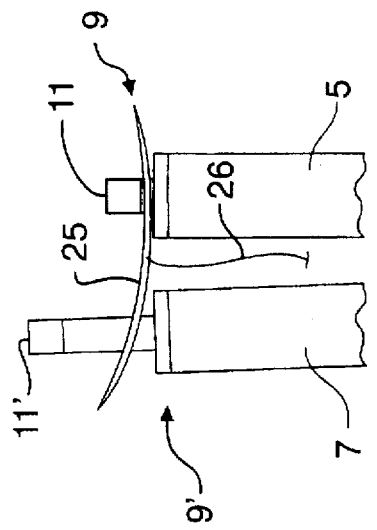
Figure 8C:
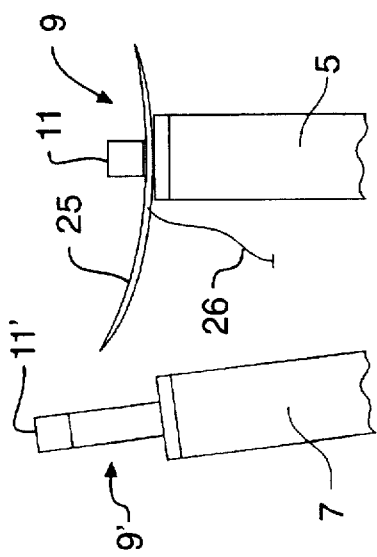
Figure 8D:
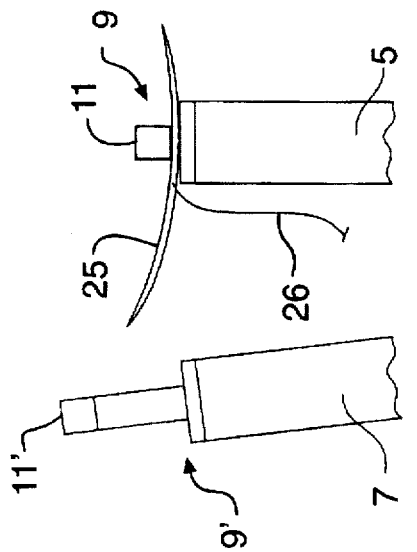
Figure 8E:
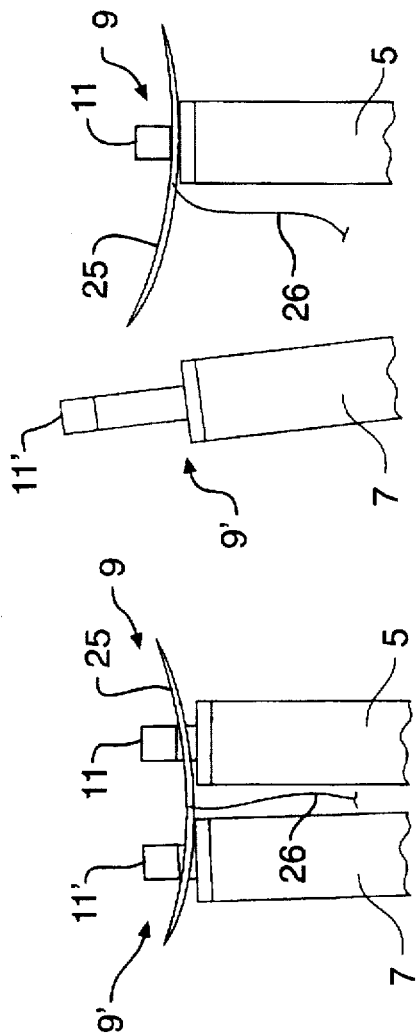
Figure 8F:
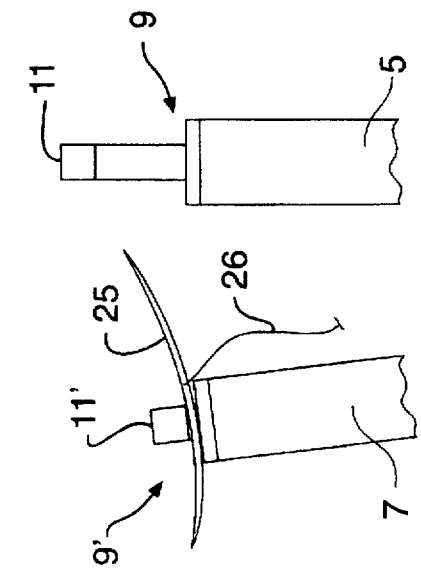

Referring now to FIGS. 8A–8F, the transfer of bowed double pointed needle 25 from arm 5 to arm 7, and back to arm 5, is illustrated in sequence. In FIG. 8A, needle 25 is held securely in needle holder 9, and arms 5 and 7 are spaced (pivoted) apart from each other. In FIG. 8B, the arms have been pivoted into the needle transfer position, with holders 9 and 9' in close proximity to each other. At this point, actuation of the proximity switch 21 causes gripping jaw 11' of needle holder 9' to move to its needle gripping position, as shown in FIG. 8C. As also seen in FIG. 8C, gripping jaw 11 remains in its gripping position for a predetermined time period after gripping jaw 11' reaches its gripping position, so as to prevent inadvertent needle droppings. In FIG. 8D the needle transfer has been completed, with gripping jaw 11 returned to its release position. In FIG. 8E, arms 5,7 and corresponding gripping jaws 11, 11' are back in the position shown in FIG 8C, as needle 25 is transferred back to arm 5. In FIG. 8F, the return needle transfer has been completed.

Figure 9:
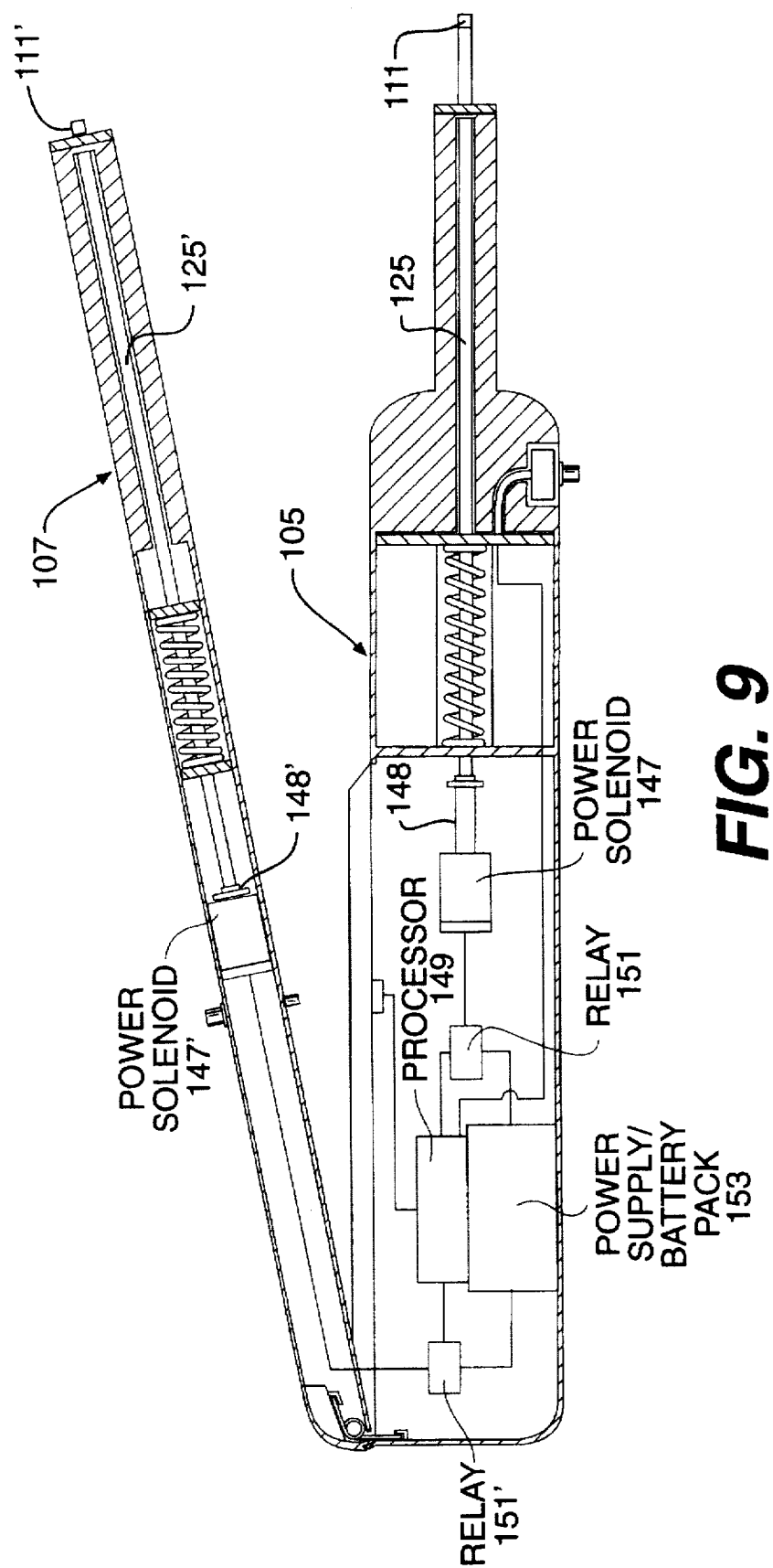
FIG. 9 illustrates a second self-contained embodiment of the invention, wherein the power actuation and electronic control components are contained within the hand graspable tool body.

A second "self-contained" embodiment of the present invention is illustrated in FIG. 9. This embodiment differs from the first embodiment in that electromechanical componentry corresponding to that housed within control box 3 (of the first embodiment) is contained within a modified hand graspable tool body 101, and control cables 41, 41' are dispensed with. As between the two embodiments, like elements are correspondingly numbered, and except as otherwise noted, the structure and operation is essentially the same.

In the self contained embodiment, solenoids 147, 147' are mounted within respective arms 105, 107, directly in line with respective jaw shanks 125, 125'. The core 148, 148' of each solenoid is directly connected with the proximal end of the corresponding jaw shank 125, 125', so as to move the gripping elements 111, 111' between their gripping and release positions. In addition to solenoid 147, primary arm 105 houses a pair of relays 151, 151', a processor 149, and a power supply 153. Power supply 153 could be provided in the form of a battery pack to allow completely portable operation.

Obviously, in the second embodiment, component miniaturization takes on greater importance. Toward this end, it is preferred that the processor of the second embodiment be provided in the form of a microprocessor chip, and that the other components be miniaturized and integrated to the extent permitted by the state of the art. In this regard, a limiting factor is that the solenoids (and power supply therefor) must have a capacity to allow reliable generation of gripping forces sufficient to securely hold a needle in the intended suturing or sewing application.

The present invention has been described in terms of exemplary and presently preferred embodiments thereof. Numerous other embodiments, modifications and variations within the scope and spirit of the appended claims will occur to those having ordinary skill in the art, upon a review of this disclosure. For example, it is not necessary that the movement of the needle holders be pivotal into and out of a needle transfer position; the motion could be rectilinear. Nor is the invention limited to needle holders in the form of vise-like clamps. Moreover, it will be appreciated that various power actuation and detector mechanisms could be provided. For example, the power actuation could be pneumatic or hydraulic instead of electromagnetic. In addition, the detector could comprise various known proximity-type switches, e.g., optical or magnetic switches.

In particular, it will be appreciated that the configuration of the device may vary considerably depending upon the uses to which the device will be put, and the manufacturing methods therefor. In this regard, the principles of the invention may, e.g., be applied to provide semi-automatic laparoscopic suturing tools, with small (needle holder carrying) arms pivoted at the end of an elongated shaft insertable into a trocar or the like.

We claim:

1. A semi-automatic suturing/sewing device, comprising:
   a hand graspable tool body;
   a pair of needle holders operably connected to said body for movement with respect to each other into and out of a preset needle transfer position, by application of manual force, each said holder comprising a releasable needle gripping element;
   a power actuator assembly providing motive forces, separate from said manual force, for actuating said gripping elements to move between respective needle gripping and release positions, and for providing a predetermined gripping force of said gripping elements in their respective gripping positions; and
   an electronic control mechanism for controlling operation of said power actuator assembly, said mechanism comprising a detector for producing a first signal when said needle holders have been moved to said needle transfer position, said control mechanism actuating said power actuator assembly in response to said first signal to automatically alternatingly hold said gripping elements in their gripping positions, and move said gripping elements to their release positions, in order to effect successive needle transfers from one needle holder to the other.

2. A semi-automatic suturing/sewing device according to claim 1, wherein said control mechanism further comprises logic control circuitry for ensuring that the release of a gripping element from its gripping position does not occur until after the other gripping element has been moved to its gripping position.

3. A semi-automatic suturing/sewing device according to claim 2, wherein said logic control circuitry generates a second signal to actuate said power actuator assembly to cause said release of one gripping element, and a third signal to actuate said power actuator assembly to cause the other gripping element to move to said gripping position, said second signal being generated a predetermined time period after generation of said third signal.

4. A semi-automatic suturing/sewing device according to claim 1, wherein said control mechanism further comprises logic control circuitry for receiving said first signal and generating second and third signals for triggering said actuation of the power actuator, the generation of said second and third signals being delayed for predetermined time periods after receipt of the first signal.

5. A semi-automatic suturing/sewing device according to claim 1, wherein said needle transfer position is a position with the needle holders in close proximity to each other, and said detector comprises a proximity switch assembly.

6. A semi-automatic suturing/sewing device according to claim 5, wherein said proximity switch assembly is adjustable to vary the needle transfer position.

7. A semi-automatic suturing/sewing device according to claim 1, wherein said hand grippable body comprises a pair of arms having ends on which said needle holders are respectively mounted, said arms being pivotally connected with respect to each other to each other such that said needle holders are pivotable into and out of said needle transfer position.

8. A semi-automatic suturing/sewing device according to claim 7, wherein said needle transfer position is a position with the needle holders pivoted into close proximity to each other, and said detector comprises a proximity switch including cooperative elements mounted on said arms, respectively.

9. A semi-automatic suturing/sewing device according to claim 8, wherein said cooperating elements comprise, respectively, a push-button switch on one of the arms, and a protruding push-pin element on the other arm for actuating said push-button switch, the protruding distance of said push-pin element being adjustable in order to vary the needle transfer position.

10. A semi-automatic suturing/sewing device according to claim 7, wherein said arms are spring biased to pivot the ends of said arms away from each other, to thereby position said needle holders out of said needle transfer position.

11. A semi-automatic suturing/sewing device according to claim 7, wherein the gripping dement of each needle holder comprises a vise jaw mounted for reciprocating movement into and out of contact with an opposing surface provided on a respective one of said arm ends.

12. A semi-automatic suturing/sewing device according to claim 11, wherein each said vise jaw is provided at the end of an elongated shank mounted for longitudinal movement within a respective one of said arms.

13. A semi-automatic suturing/sewing device according to claim 12, wherein said power actuator assembly comprises a pair of electric solenoids, each said solenoid being operably connected with a respective one of said elongated shanks and serving to actuate movement of a respective one of said vise jaws.

14. A semi-automatic suturing/sewing device according to claim 13, wherein said solenoids are located remote from said hand graspable body and are connected with respective ones of said elongated shanks by flexible control cables.

15. A semi-automatic suturing/sewing device according to claim 14, wherein each of said shanks is connected with a return spring mounted within a respective one of said arms, for ensuring return of the vise jaws to the release position on deactivation of the respective solenoid.

16. A semi-automatic suturing/sewing device according to claim 13, wherein said electronic control mechanism comprises a digital processor for receiving said first signal from the detector and generating a pair of output signals based thereon which are transmitted to a pair of electrical relays in order to control the supply of power to said solenoids.

17. A semi-automatic suturing/sewing device according to claim 1, wherein said power actuator assembly and said electronic control mechanism are located remotely from said hand graspable body.

18. A semi-automatic suturing/sewing device according to claim 1, wherein said power actuator assembly and said electronic control mechanism are contained within said hand graspable body.

* * * * *